United States Patent [19]

Fetters

[11] 4,254,894
[45] Mar. 10, 1981

[54] APPARATUS FOR DISPENSING A STRIPED PRODUCT AND METHOD OF PRODUCING THE STRIPED PRODUCT

[75] Inventor: Thomas T. Fetters, Lombard, Ill.

[73] Assignee: The Continental Group, Inc., New York, N.Y.

[21] Appl. No.: 69,147

[22] Filed: Aug. 23, 1979

[51] Int. Cl.³ .............................................. B65D 35/28
[52] U.S. Cl. ...................................... 222/1; 222/131; 222/386.5
[58] Field of Search ...................... 222/386.5, 389, 92, 222/94–95, 145, 136, 129, 1, 131; 426/115, 116

[56] References Cited

U.S. PATENT DOCUMENTS

| 1,760,773 | 5/1930 | Penney | 222/92 X |
| 2,569,938 | 10/1951 | Gonzalez | 222/136 |
| 2,636,644 | 4/1953 | Taylor | 222/92 |
| 3,606,809 | 9/1971 | Chambers | 222/95 |
| 3,667,653 | 6/1972 | Morane et al. | 222/145 |
| 4,062,475 | 12/1977 | Harris et al. | 222/386.5 X |

FOREIGN PATENT DOCUMENTS 2344782 3/1974 Fed. Rep. of Germany ........... 222/564
1385734 2/1975 United Kingdom .

Primary Examiner—Charles A. Marmor
Attorney, Agent, or Firm—Charles E. Brown

[57] ABSTRACT

A product to be dispensed is packaged in an axially collapsible product bag in distinct transversely extending axial layers. When the product is dispensed, it enters into a discharge nozzle generally from the center of the bag with the result that there is an almost immediate combining of the product layers to be simultaneously dispensed in a striped stream.

8 Claims, 3 Drawing Figures

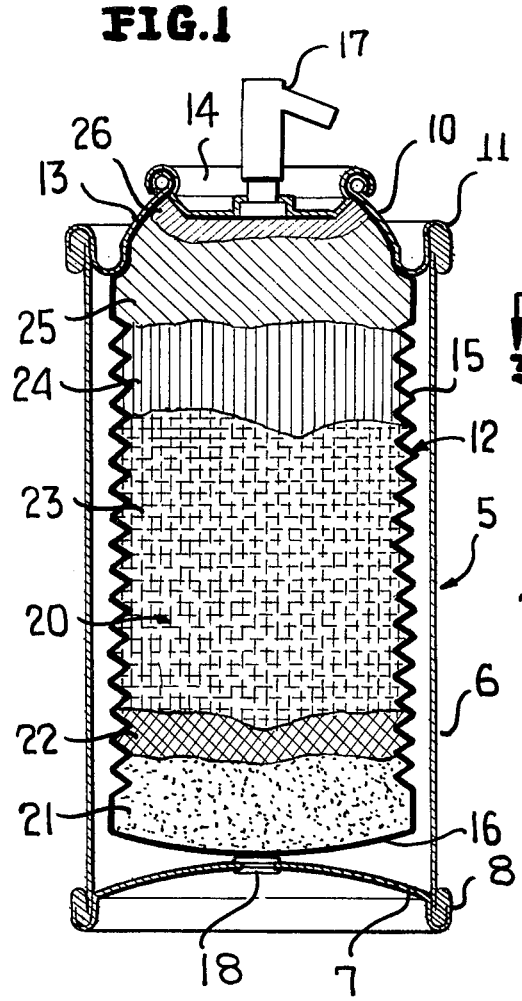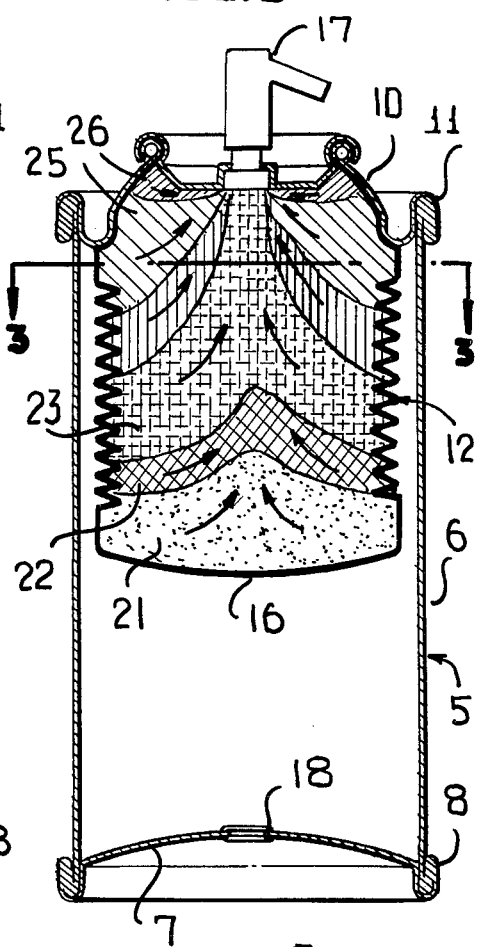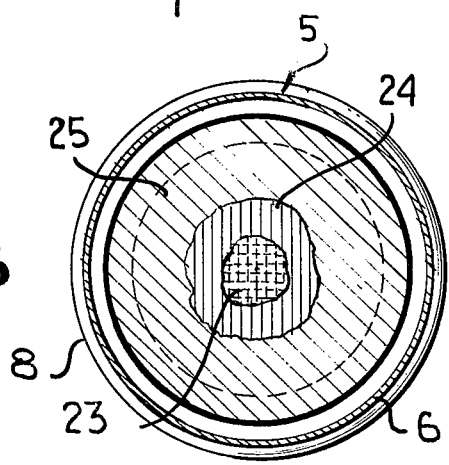

APPARATUS FOR DISPENSING A STRIPED PRODUCT AND METHOD OF PRODUCING THE STRIPED PRODUCT

This invention relates in general to new and useful improvements in the packaging of flowable products in readily dispensing containers, and more particularly to the packaging of a flowable product in discrete layers within a collapsible bag for the purpose of dispensing a striped product.

It is well known to place a product in a dispensing container having a collapsible compartment defined by an axial collapsible bag. The U.S. Patent No. 3,433,391 to Krizka et al, granted March 18, 1969, discloses such a container.

The Krizka et al container functions in the desired manner. However, a single product is placed in the collapsible bag in accordance with the Krizka et al disclosure and the stream of the dispensed product is of a uniform consistency, flavor and color.

There are many instances where it is desired to make the product attractive by varying the color. Certain toothpastes, when dispensed, have a candy stripe appearance.

It is also conventional to have multi-flavored foods. Further, it is well known to have food products which are a combination of several individual foods.

In accordance with this invention, it is proposed to fill a conventional product bag with a product or products arranged in layers within that bag, the layers differentiating from one another by at least one of color, flavor, texture and product composition. It has been found that when the bag containing the product in such layers is axially collapsed in the normal manner and wherein the dispensing valve is at the center of the dispensing end of the bag, the product flows toward the center of the bag and then axially out through the dispensing valve so that the resultant product flow is a combination of a plurality of adjacent layers arranged in concentric relationship.

By making the product layers of selected thicknesses, various arrangements can be obtained with the dispensed product and as many as three distinct layers can be simultaneously dispensed.

With the above and other objects in view that will hereinafter appear, the nature of the invention will be more clearly understood by reference to the following detailed description, the appended claims, and the several views illustrated in the accompanying drawings.

IN THE DRAWINGS:

FIG. 1 is an axial sectional view taken through a dispensing container having disposed therein a product arranged in transversely extending axial layers in accordance with this invention.

FIG. 2 is a sectional view similar to FIG. 1, and shows the manner in which the various layers flow out through the dispensing nozzle to form a multilayered dispensed stream.

FIG. 3 is a transverse sectional view taken generally along the line 3—3 of FIG. 2, and shows the arrangement of the various layers of the product adjacent the dispensing nozzle.

Referring now to the drawings in detail, it will be seen that there is illustrated in FIG. 1 a conventional dispensing container generally identified by the numeral 5. The dispensing container 5 is formed in accordance with the teaching of the Krizka et al patent 3,433,391, and includes a can body 6 closed at its upper end by an end unit 7 secured to the body 6 by a conventional double seam 8. The upper end of the can body 6 is closed by an end unit 10 which is secured to the body 6 by another double seam 11.

A product bag 12 is disposed within the container 5 and has a reduced neck portion 13 which is sealed at its upper end in the connection between a valve cup 14 and the end unit 10. The product bag 12 is especially constructed and includes a corrugated or pleated body wall 15 which permits endwise or axial collapsing only of the product bag 12. The product bag 12 also includes a bottom wall 16.

The container 5 further includes a conventional dispensing valve 17 which is carried by the valve cup 14 and which is in communication with the interior of the product bag 12 for receiving a product from therewithin.

The end unit 7 is provided with a filling opening closed by a plug 18 whereby the space within the container 5 surrounding the product bag 12 may be filled with a suitable gas under pressure. While this gas under pressure acts entirely around the bag 12, the collapsing of the bag as a product therein is dispensed is an endwise or axial one, as is best shown in FIG. 2.

This invention most particularly relates to the placement of the product therein. As is clearly shown in FIG. 1, the product, which is generally identified by the numeral 20, is placed within the product bag 12 in a series of distinct layers 21, 22, 23, 24, 25 and 26. The layers 21-26 are distinct transversely extending axial layers. Depending upon the desired product, each of the layers 21-26 may be composed of the same product but wherein the layers are differently colored. On the other hand, the product layers may be differently flavored or of a different texture. Finally, the product layers may be actually of different products. Any combination of the four above-identified differences may be employed.

In order to obtain an immediate mixing of the product layers, the uppermost product layer 26 is made thin as compared to the thicknesses of the other product layers. Thus, as soon as the dispensing valve 17 is actuated, after an initial stream of the product layer 26, the stream will have at least a two-layer composition with the two-layer composition changing to a three-layer composition as the dispensing continues.

No attempt is made here to indicate possible arrangements of the product layers. It will be understood, however, that the product layers may be so arranged that the dispensed product stream may have a constant core surrounded by one or more annular product rings and that the various product layers may be repeated within the product bag 12. On the other hand, the makeup of the dispensed product stream may constantly vary as the product is dispensed, changing from one combination at the beginning to another, then another, etc.

The specific products which can be dispensed may vary over a large range. The products may vary from toothpaste to colored whipped cream, to cake decorations, etc. It is also feasible that the products be other than edible products and possibly could be a combination of paint coloring and such things as chemically reactive adhesive components.

Although only a preferred embodiment of the invention has been specifically illustrated and described herein, it is to be understood that the dispensing container may be of a different construction and that the product may be greatly varied.

I claim:

1. An apparatus for dispensing a striped product, said apparatus comprising a rigid container, a collapsible bag mounted within said rigid container, a dispensing valve carried by said rigid container in communication with the interior of said collapsible bag for dispensing the contents thereof, a product in said collapsible bag, and a gas in said rigid container around said collapsible bag for exerting a collapsing pressure on said collapsible bag to force said product towards said dispensing valve; the improvement residing in said product being arranged in said collapsible bag in distinct transversely extending axial layers, there being a single outlet passage between said collapsible bag and said dispensing valve and said collapsible bag being collapsible primarily in an axial direction.

2. The apparatus of claim 1 wherein said product layers are composed of products selectively different in at least color, taste, texture and composition.

3. The apparatus of claim 2 wherein that one of said product layers disposed immediately adjacent said dispensing valve is thinner in height than at least the next adjacent one of said product layers.

4. The apparatus of claim 1 wherein that one of said product layers disposed immediately adjacent said dispensing valve is thinner in height than at least the next adjacent one of said product layers.

5. The apparatus of claim 1 wherein said collapsible bag has a pleated body for effecting said endwise collapse.

6. A method of dispensing a striped product, said method comprising the steps of providing an axially collapsible bag having at one end thereof a centrally located dispensing valve, filling the bag with a flowable product arranged in the bag in distinct transversely extending axial layers, and applying a collapsing force to the bag while actuating the dispensing valve to effect discharge of the product from a radially central part only of the bag through a single dispensing opening with product portions of adjacent ones of the layers being simultaneously dispensed.

7. The method of claim 6 wherein said product layers are composed of products selectively different in at least color, taste, texture and composition.

8. The method of claim 6 wherein said collapsing force is applied by a surrounding gaseous pressure.

* * * * *